(12) United States Patent
Thornton (10) Patent No.: US 8,257,267 B2
(45) Date of Patent: Sep. 4, 2012

(54) SELF-ALIGNING IVUS CATHETER ROTATIONAL CORE CONNECTOR

(75) Inventor: Peter Thornton, Los Altos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1086 days.

(21) Appl. No.: 11/621,356

(22) Filed: Jan. 9, 2007

(65) Prior Publication Data

US 2008/0167560 A1   Jul. 10, 2008

(51) Int. Cl.
*A61B 8/14* (2006.01)

(52) U.S. Cl. ........ 600/467; 600/437; 600/459; 600/462; 606/1

(58) Field of Classification Search .................. 600/407, 600/437, 443, 450, 454, 459, 462, 463, 466–468; 604/264, 528, 533, 535; 606/167–171, 180; 439/8, 9, 11, 374, 378, 379
See application file for complete search history.

(56) References Cited

U.S. PATENT DOCUMENTS

| | | |
|---|---|---|
| 4,243,884 A | 1/1981 | Avera, Jr. |
| 4,362,166 A | 12/1982 | Furler et al. |
| 4,407,298 A | 10/1983 | Lentz et al. |
| 5,150,715 A | 9/1992 | Ishiguro et al. |
| 5,178,159 A | 1/1993 | Christian |
| 5,348,481 A | 9/1994 | Ortiz |
| 5,353,798 A | 10/1994 | Sieben |
| 5,377,682 A | 1/1995 | Ueno et al. |
| 5,383,460 A | 1/1995 | Jang et al. |
| 5,544,660 A | 8/1996 | Crowley |
| 5,715,825 A | 2/1998 | Crowley |
| 5,794,715 A | 8/1998 | Norman |
| 5,810,859 A | 9/1998 | DiMatteo et al. |
| 5,902,245 A | 5/1999 | Yock |
| 5,957,941 A | 9/1999 | Ream |

(Continued)

FOREIGN PATENT DOCUMENTS

EP   1026982 B1   11/2005

(Continued)

OTHER PUBLICATIONS

Official Communication for U.S. Appl. No. 12/464,280 mailed Sep. 14, 2011.

(Continued)

*Primary Examiner* — Tse Chen
*Assistant Examiner* — Mark Remaly
(74) *Attorney, Agent, or Firm* — Frommer Lawrence & Haug LLP; Patrick R. Turner (57) ABSTRACT

The present invention provides self-aligning rotational connectors. In an non-limiting embodiment, a catheter system comprises a catheter connectable to a drive unit. The catheter includes a rotator, and at least one orientating feature extending proximally from the rotator, and configured to be inserted into an orienting slot of a shaft connector of the drive unit. When the orienting feature is inserted into the slot of the shaft connector, the slot transmits torque from the shaft connector to the orientating feature, and therefore the rotator of the catheter. Electrical contacts are provided on the rotator and the shaft connector, wherein the contacts of the rotator are properly aligned with and engage the contacts of the shaft connector. Further, the shaft connector has a slopping surface that slops downward into the slot for automatically aligning the rotator rotationally with the shaft connector during insertion of the catheter into the drive unit.

31 Claims, 7 Drawing Sheets

U.S. PATENT DOCUMENTS

| | | | |
|---|---|---|---|
| 5,971,923 | A | 10/1999 | Finger |
| 5,971,991 | A | 10/1999 | Sunderland |
| 6,050,949 | A | 4/2000 | White et al. |
| 6,063,035 | A | 5/2000 | Sakamoto et al. |
| 6,244,882 | B1 | 6/2001 | Greenstein |
| 6,261,246 | B1 | 7/2001 | Pantages et al. |
| 6,264,613 | B1 | 7/2001 | Pfeiffer et al. |
| 6,309,358 | B1 | 10/2001 | Okubo |
| 6,319,227 | B1 | 11/2001 | Mansouri-Ruiz |
| 6,461,199 | B1 | 10/2002 | Koga et al. |
| 6,485,482 | B1 | 11/2002 | Belef |
| 6,508,781 | B1 | 1/2003 | Brennan et al. |
| 6,529,760 | B2 | 3/2003 | Pantages et al. |
| 6,530,887 | B1 | 3/2003 | Gilbert et al. |
| 6,714,809 | B2 | 3/2004 | Lee et al. |
| 6,770,058 | B1 | 8/2004 | Liprie |
| 6,814,727 | B2 | 11/2004 | Mansouri-Ruiz |
| 7,004,787 | B2 | 2/2006 | Milan |
| 7,530,953 | B2 | 5/2009 | Harshman et al. |
| 2003/0073348 | A1 | 4/2003 | Ries et al. |
| 2003/0143895 | A1 | 7/2003 | Sommer et al. |
| 2004/0230123 | A1 | 11/2004 | White et al. |
| 2005/0043618 | A1 | 2/2005 | Mansouri-Ruiz |
| 2005/0251035 | A1 | 11/2005 | Wong et al. |
| 2005/0283140 | A1* | 12/2005 | Jensen et al. ............ 606/1 |
| 2007/0021685 | A1 | 1/2007 | Oepen et al. |
| 2007/0178767 | A1* | 8/2007 | Harshman et al. ............ 439/660 |
| 2007/0178768 | A1 | 8/2007 | Harshman et al. |
| 2009/0221918 | A1 | 9/2009 | Harshman et al. |

FOREIGN PATENT DOCUMENTS

| | | |
|---|---|---|
| JP | 6133973 | 5/1994 |
| JP | H09-239083 | 9/1997 |
| JP | 11332866 | 12/1999 |
| WO | WO-0007500 | 2/2000 |
| WO | 2006026439 | 3/2006 |

OTHER PUBLICATIONS

Official Communication for U.S. Appl. No. 12/464,280 mailed Mar. 30, 2012.

Official Communication for U.S. Appl. No. 11/669,752 mailed Jun. 13, 2007.

Official Communication for U.S. Appl. No. 11/669,752 mailed Nov. 19, 2007.

Official Communication for U.S. Appl. No. 11/669,752 mailed Jun. 19, 2008.

Official Communication for U.S. Appl. No. 11/669,752 mailed Jan. 5, 2009.

* cited by examiner

SELF-ALIGNING IVUS CATHETER ROTATIONAL CORE CONNECTOR

FIELD OF THE INVENTION

The present invention relates to catheters, and more particularly to self-aligning rotational core connectors for catheters.

BACKGROUND INFORMATION

Intravascular ultrasound imaging systems (IVUS) are used to obtain ultrasound images inside a patient's body. An IVUS system typically includes an ultrasound catheter having a flexible catheter body adapted for insertion into the vascular system of the patient. To obtain ultrasound images, the catheter comprises an imaging core received within a lumen of the catheter body. The imaging core comprises an ultrasound transducer connected to the distal end of a flexible drive cable that extends to the proximal end of the catheter through the catheter lumen. The drive cable is used to rotate and longitudinally translate the transducer within the catheter lumen. The catheter includes electrical and mechanical connectors for electrically and mechanically connecting the catheter to a motor drive unit (MDU). The MDU includes a motor for rotating the imaging core, and transmits electrical signals to and from the transducer.

Currently two types of connections are used to connect the catheter to the MDU. The first type uses a stationary connector in which the rotating wiring of the transducer is converted to stationary wiring by means of a rotary transformer, slip ring or capacitive device housed in a catheter hub. Disadvantages of this approach include increased cost, increased hub size, and increased complexity. Because a rotary transformer or slip ring is installed in each catheter, there is the additional cost of purchasing or manufacturing the transformer or slip ring for each catheter as well as the additional labor cost for assembly. Also, the rotary transformer must be accommodated in the catheter hub, and as other signals are added, the size of the transformer, and hence the hub, may have to be enlarged. A catheter with a rotary transformer is more complex and requires that the fit of the components be within close-tolerances to perform this type of catheter cannot be tested until final assembly, at which time, if there is a problem with the catheter, the entire unit must be strapped.

The second type of connection uses a coaxial-type connector in which the mating contacts comprise a center pin and concentric spring loaded rings so that the catheter and MDU are properly mate regardless of the relative position of their connectors. The rotary transformer or slip ring that converts the rotating wiring to stationary wiring is house in the MDU. Disadvantages of this approach include limitations in the number of contacts available, greater complexity, and the potential for slippage in the mechanical coupling. The cost of the multiple contact coaxial connector can approach that of the rotary transformer. For more than two contacts, the coaxial connector becomes larger, complex, and expensive. Typically the contacts of the coaxial connector act as a mechanical coupling to transmit torque from the motor drive to the rotating portion of the catheter, and as the contacts in the motor drive wear, slippage can occur.

Therefore, there is a need for improved rotational connectors that overcome disadvantages of the prior art.

SUMMARY OF THE INVENTION

The present invention provides self-aligning rotational connectors for catheters and other applications were rotational alignment of mating connectors is desired without the need for manual alignment.

In an embodiment, a catheter system comprises a catheter connectable to a drive unit. The catheter includes an imaging core, a rotator coupled to a proximal end of the imaging core, and at least one orientating feature extending proximally from the rotator. The drive unit includes a shaft connector having at least one orienting slot, wherein the orienting feature of the catheter is configured to be inserted into the slot. When the orienting feature is inserted into the slot of the shaft connector, the rotator and imaging core rotate with the shaft connector, and the slot transmits torque from the shaft connector to the orientating feature, and therefore rotator and imaging core. Electrical contacts are provided on the rotator and the shaft connector. When the orienting feature is inserted into the slot of the shaft connector, the electrical contacts of the rotator are properly aligned with and engage the electrical contacts of the shaft connector. Further, the shaft connector has a slopping surface that slopes downward into the slot. During insertion of the catheter into the drive unit, the orienting feature engages the slopping surface of the shaft connector causing the shaft connector to automatically rotate. As the shaft connector rotates, the orientation feature slides down the slopping surface and into the slot, at which point the rotator is properly aligned rotationally with the shaft connector.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

In order to better appreciate how the above-recited and other advantages and objects of the present inventions are objected, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION

Figure 1:
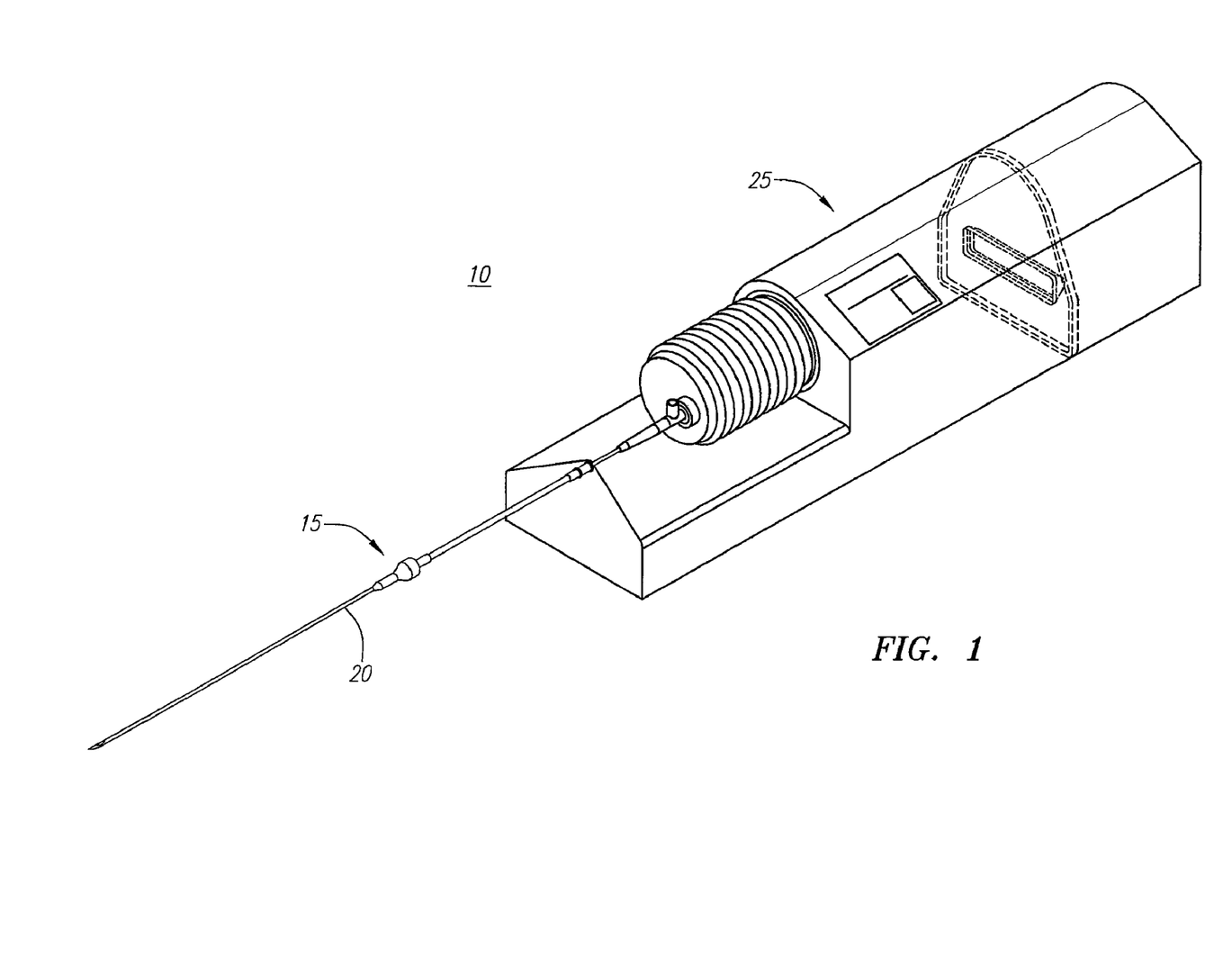
FIG. 1 is a perspective view of a catheter system in accordance with an embodiment of the invention.

FIG. 1 shows an exemplary catheter ultrasound imaging system 10 according to an embodiment of the invention. The imaging system 10 includes a catheter 15 adapted for insertion into the vascular system of a patient. The catheter 15 includes a flexible elongated catheter body 20 and an imaging core (not shown) within a lumen in the catheter body 20. The imaging core comprises an ultrasound transducer, e.g., piezoelectric crystal (PZT), connected to the distal end of a drive cable, which extends through the catheter body 20. The drive cable is used to rotate and longitudinally translate the transducer within the catheter 15. The proximal end of the catheter 15 is detachably connected to a motor drive unit (MDU) 25, which houses a motor for rotating the imaging core.

Figure 2A:
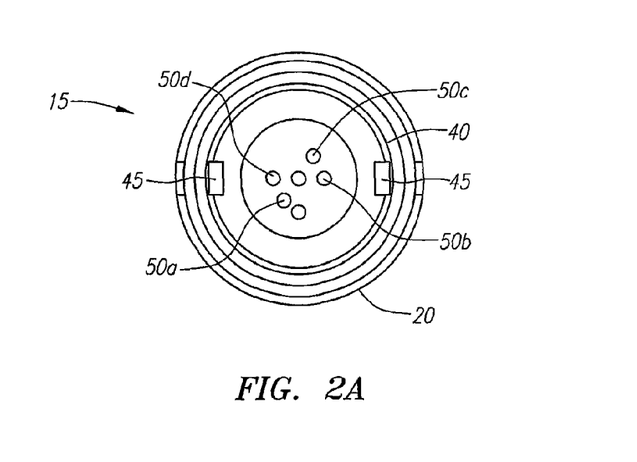
FIG. 2A is a back view of the proximal end of a catheter in accordance with an embodiment of the invention.
Figure 2B:
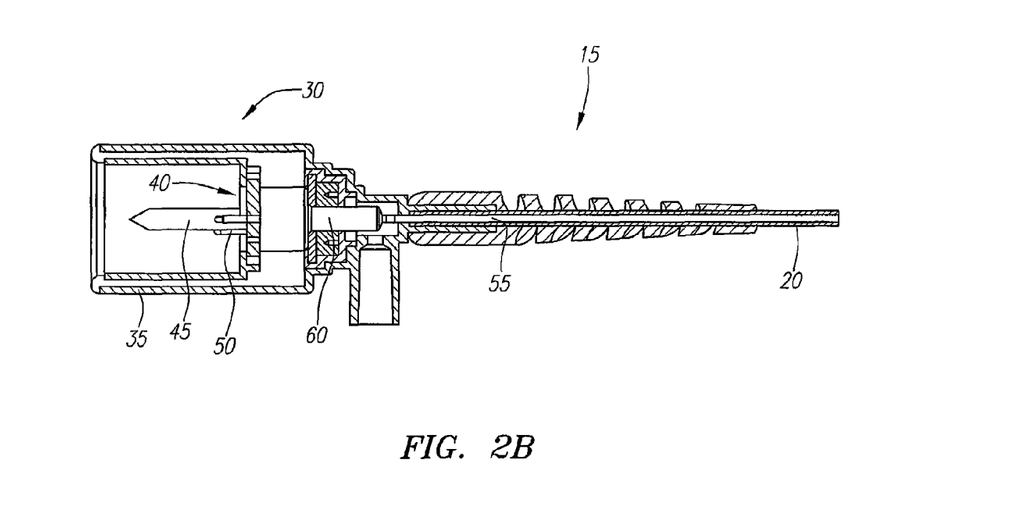
FIG. 2B is a cross-sectional side view of the proximal end of a catheter in accordance with an embodiment of the invention.

Referring to FIG. 2B, the catheter 15 includes a catheter hub 30 at its proximal end for mechanically and electrically connecting the catheter 15 to the MDU 25. The catheter hub 30 includes a non-rotating housing 35 and a rotator or rotating element 40 housed within the non-rotating housing 35. The rotator 40 rotates within the non-rotating housing 35. The catheter 15 includes orienting features 45 in the from of splines extending from the rotator 40. The catheter 15 also include electrical contacts 50 on the rotator 40 for electrically coupling the catheter 15 to the MDU 25. In this embodiment, the contacts 50 are in the form of connector pins extending from the rotator 40. The catheter 15 further includes a stamped shaft 60 connecting the rotator 40 to the proximal end of the drive cable 55, and a seal around the shaft 60. The connector pins 50 are electrically coupled to the transducer of the imaging core via wires or coaxial cable (not shown) running through the shaft 60 and drive cable 55. The connector pins 50 provide the electrical interface between the catheter 15 and the MDU 25 by inserting the pin connectors 50 into a female connector, e.g., sockets, in the MDU 25, as explained further below. As shown in FIG. 2A, the orientating splines 45 extend from opposite sides of the rotator 40. Each spline 45 each has a sharp leading edge centered along the width of the spline 45.

Figure 3A:
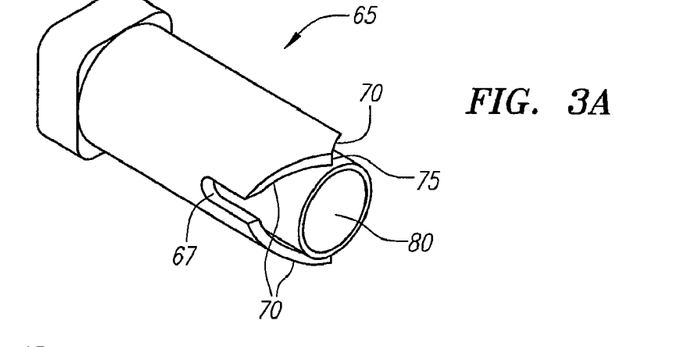
FIG. 3A is a perspective view of a two-slotted shaft connector in accordance with an embodiment of the invention.
Figure 3B:
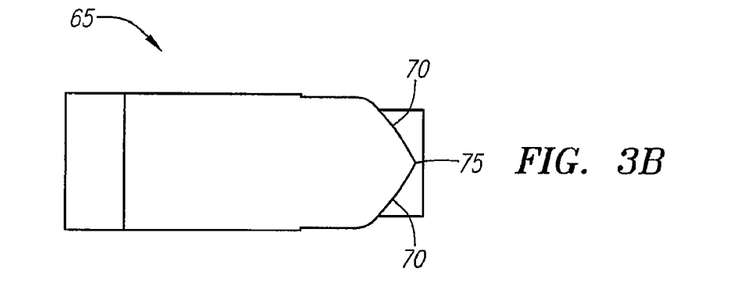
FIG. 3B is a top view of a two-slotted shaft connector in accordance with an embodiment of the invention.
Figure 3C:
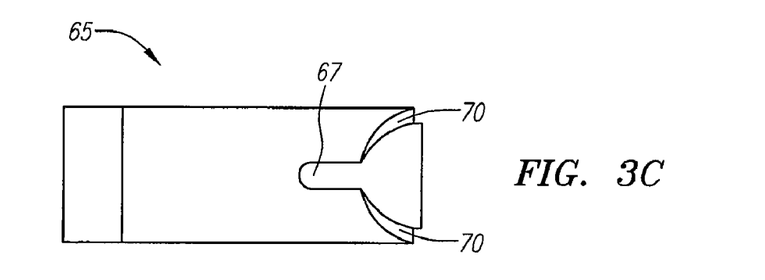
FIG. 3C is a side view of a two-slotted shaft connector in accordance with an embodiment of the invention.
Figure 3D:
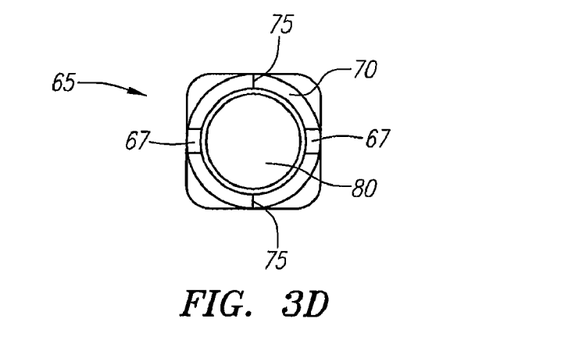
FIG. 3D is a front view of a two-slotted shaft connector in accordance with an embodiment of the invention.

FIGS. 3A-3D show a shaft connector 65 of the MDU 25 according to an embodiment of the invention. The proximal end of the shaft connector 65 is connected to the motor (not shown) of the MDU 25, which rotates the shaft connecter 65. The shaft 65 includes two outer orienting slots 67 at opposite sides. The orienting splines 45 of the catheter 15 are configured to fit into the orienting slots 67 of the shaft connector 65. The shaft connector 65 further includes outer beveled surfaces 70 that slope downward into the orienting slots 67. As shown in FIG. 3C, each orientating slot 67 has two beveled surfaces 70 that slope into the slot 67 from opposite sides of the slot 67. FIG. 3B shows a top view of the shaft connector 65, in which the beveled surfaces 70 of the slots meet at sharp leading edges 75 centered between the slots 67. The female connector, e.g., sockets, of the MDU 25 is housed within the shaft connector 65 and is accessible though an opening 80 in the shaft connector 65. The female connector is configured so that it is properly aligned with the connector pins 50 of the catheter 15 when the splines 45 of the catheter 15 are inserted into the slots 67 of the shaft connector 65.

Figure 4:
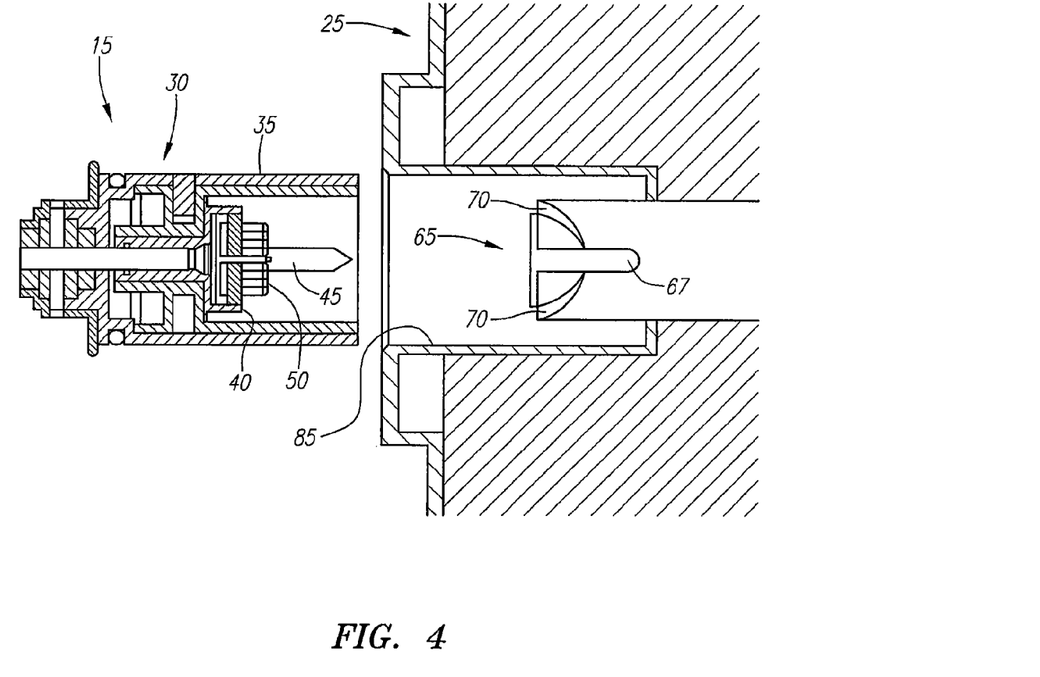
FIG. 4 is a cross-sectional view of the proximal end of a catheter and a motor drive unit in accordance with an embodiment of the invention.

Referring to FIG. 4, insertion of the catheter hub 30 into the MDU 25 will now be described. As shown in FIG. 4, the shaft connector 65 is positioned within a port 85 of the MDU configured to receive the catheter hub 30 therein. The catheter hub 30 is inserted into the port 85 of the MDU 25 such that the non-rotating housing 35 of the hub 30 sits firmly in the port 85. The non-rotating housing 35 is locked in place in the port 85 of the MDU 25. As the catheter hub 30 is inserted into the port 85, the leading edges of the splines 45 reach the beveled surfaces 70 of the shaft connector 65. As the hub 30 continues to be inserted into the port 85, the engagement between the splines 45 and the beveled surfaces 70 of the shaft connector 65 converts the longitudinal insertion force exerted by the splines 45 into rotational force that causes the shaft connector 65 to rotate. The longitudinal insertion force is applied in a direction substantially parallel to the rotation axis of the shaft connector 65. As the shaft connector 65 is rotated, the leading edges of the splines 45 slide down the beveled surfaces 70 of the shaft connector 65 and into the slots 67 of the shaft connector 65, at which point the connector pins 50 are properly aligned with the connector in the shaft 65. As the hub 30 continues to be inserted into the port 85, the splines 45 slide longitudinally into the respective slots 67, and the connector pins 50 of the hub 30 are inserted into the connector in the shaft 65 through the shaft opening 80. Preferably, the splines 45, slots 67 and beveled surfaces 70 are configured so that the connector pins 50 of the hub do not begin to engage the connector of the MDU until the full width of each spline 45 is in the respective slot 67. This ensures that the connector pins 50 of the hub are properly aligned with the connector of the MDU before they engage each other.

Figure 5:
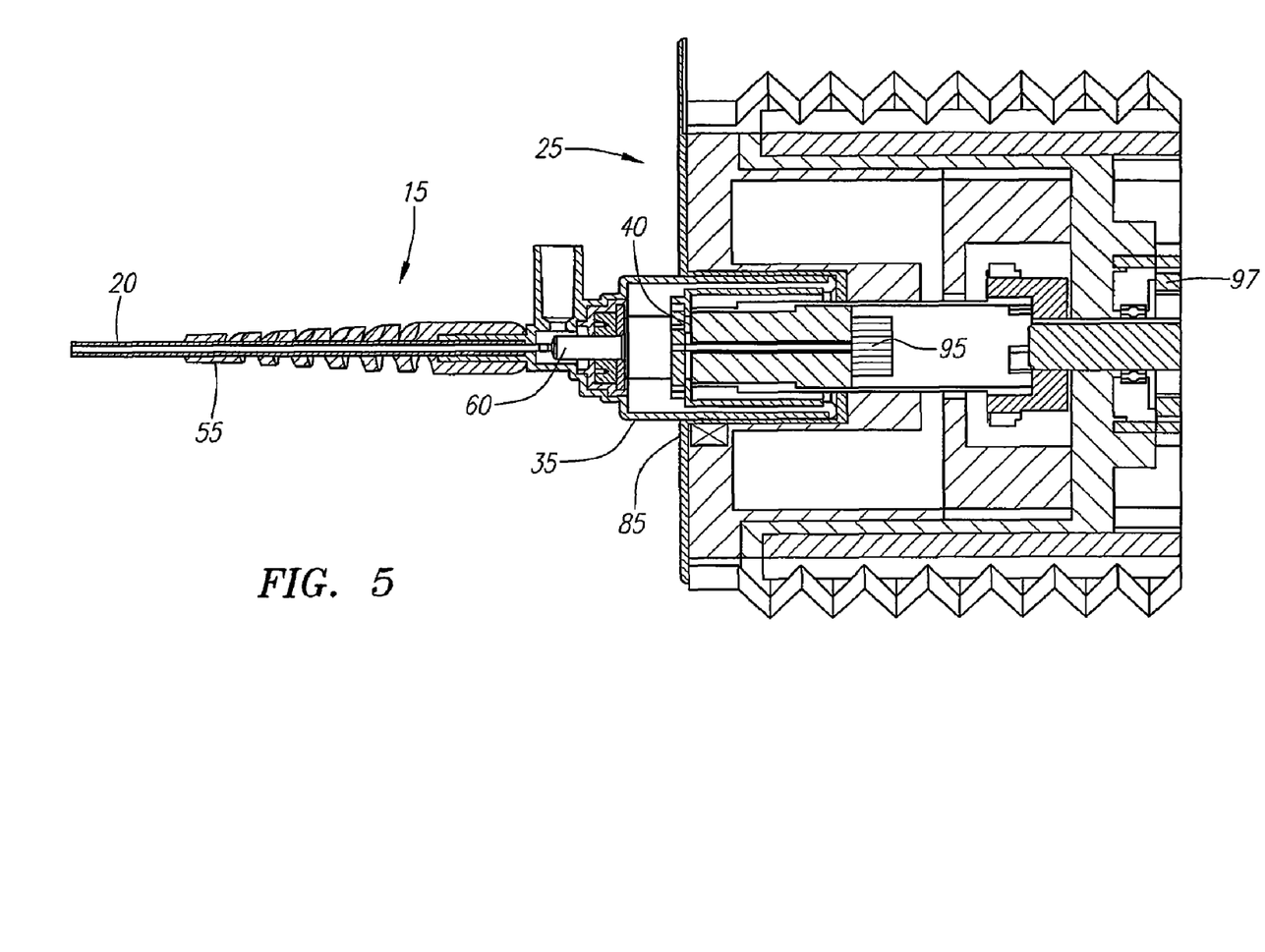
FIG. 5 is a cross-section view of the catheter connected to the motor drive unit in accordance with an embodiment of the invention.
Figure 6A:
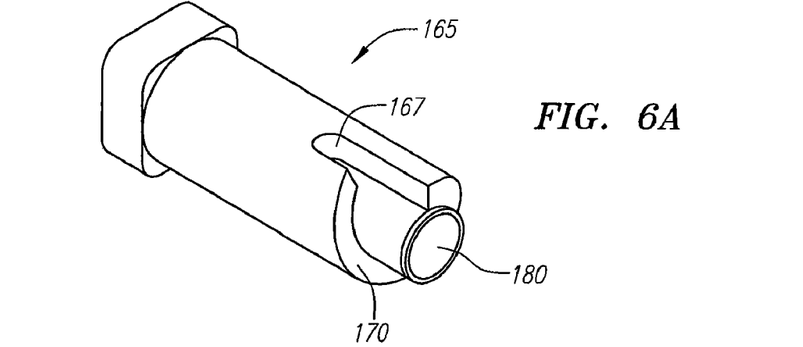
FIG. 6A is a perspective view of a one-slotted shaft connector in accordance with an embodiment of the invention.
Figure 6B:
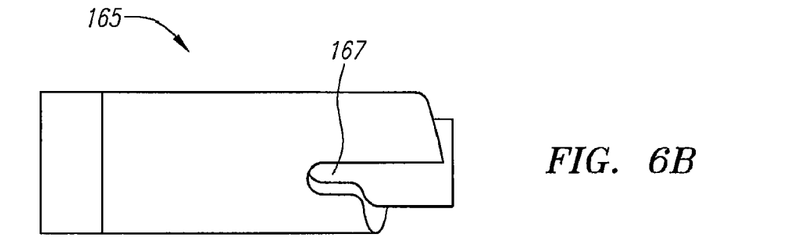
FIG. 6B is a top view of a one-slotted shaft connector in accordance with an embodiment of the invention.
Figure 6C:
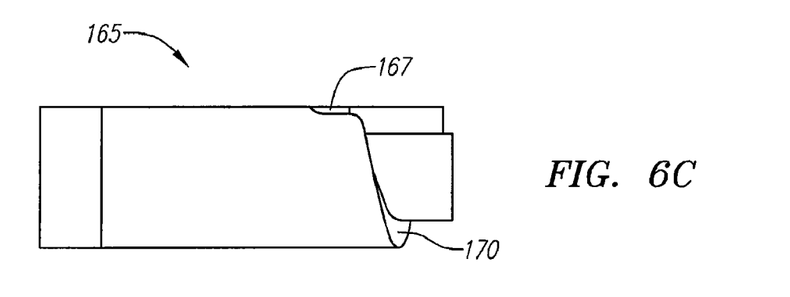
FIG. 6C is a side view of a one-slotted shaft connector in accordance with an embodiment of the invention.
Figure 6D:
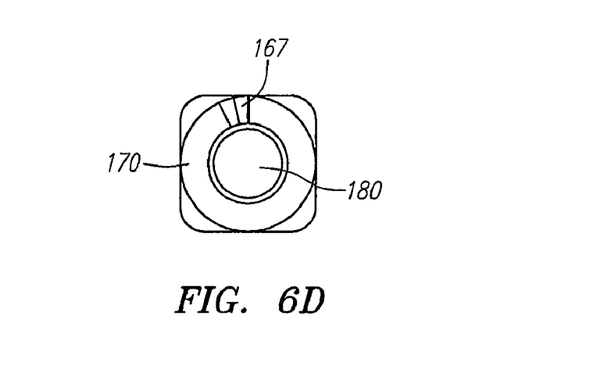
FIG. 6D is a front view of a one-slotted shaft connector in accordance with an embodiment of the invention.
Figure 7A:
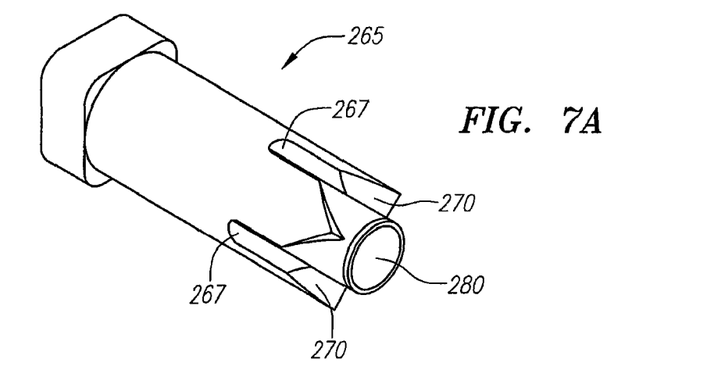
FIG. 7A is a perspective view of a four-slotted shaft connector in accordance with an embodiment of the invention.
Figure 7B:
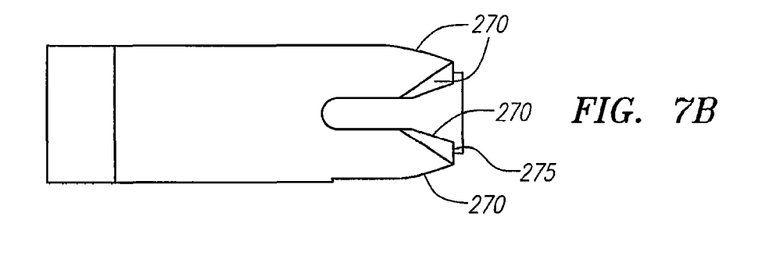
FIG. 7B is a top view of a four-slotted shaft connector in accordance with an embodiment of the invention.
Figure 7C:
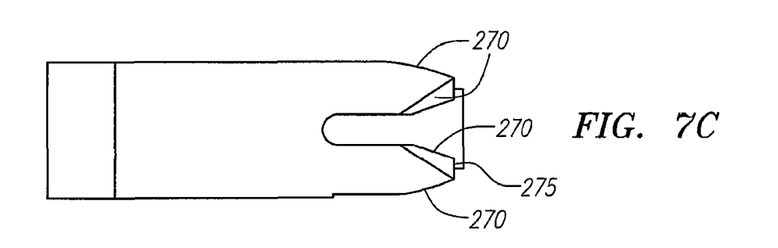
FIG. 7C is a side view of a four-slotted shaft connector in accordance with an embodiment of the invention.
Figure 7D:
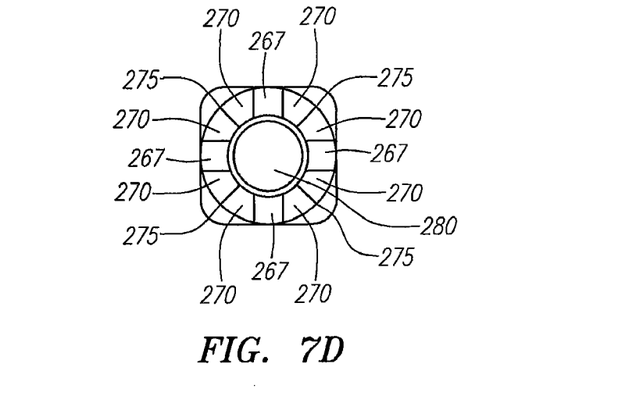
FIG. 7D is a front view of a four-slotted shaft connector in accordance with an embodiment of the invention.

FIG. 5 shows the catheter hub 30 fully inserted into the MDU 25. As shown in FIG. 5, the MDU includes a female connector 95, a drive shaft for connecting the shaft connector 65 to the motor (not shown) of the MDU 25, and a rotary transformer 97 for electrically coupling the rotating wiring of the shaft to stationary wiring in the MDU 25. Other means may be used to couple the rotating wiring of the shaft to stationary wiring in the MDU 25 including slip rings and capacitors. The connector pins 50 of the hub inserted into the female connector of the MDU 25 provide electrical coupling between the imaging core of the catheter 15 and the MDU 25 electronics. Other types of connectors may be used to electrically couple the catheter hub 30 to the MDU 25. For example, the connector pins may be placed in the MDU, and the female connector in the catheter hub. Further, non-pin connectors may be used. The splines 45 inserted into the slots 67 provide mechanical coupling between the shaft connector 65 of the MDU and the drive cable 55 of the imaging core. As the shaft connector 65 is rotated by the motor of the MDU, the slots 67 of the shaft connector 65 transmit torque to the splines 45, which in turn transmit the torque to the drive cable 55 of the imaging core. Thus, the splines 45 in the slots 67 provide the rotational driving force to the imaging core, thereby reducing mechanical stress on the connector pins 50.

Referring to FIG. 2A, the rotator 40 in the hub 30 comprises duplicate pairs of connector pins 50, wherein the connector pins 50 in each duplicate pair are shorted together. For example, connector pins 50b and 50d both connect to the negative polarity of the transducer, and connector pins 50a and 50c both connect to the positive polarity of the transducer. This is done because there are two possible rotational alignments of the rotator 40 to the shaft connector 65 when the catheter 15 is connected to the MDU 25 depending on which spline 45 goes into which slot 67. These two possible rotational alignments are oriented 180 degrees apart. The duplicate connector pins 50 are positioned on the rotator such that the pattern of connector pins 50 is the same for both possible rotational alignments. This is done by orienting the connector pins 50 of a duplicate pair 180 degrees apart with respect to the rotational axis of the rotator 40. In FIG. 2A, for example, the pattern of positive polarity connector pins 50a and 50c and negative polarity connector pins 50b and 50c is the same when the rotator 40 is rotated 180 degrees. The shaft connector 65 of the MDU has corresponding duplicate sockets (not shown). Thus, proper electrical coupling is made for both possible rotational alignments.

The catheter hub and shaft can have any number of splines and slots, respectively. For example, FIGS. 6A-6D show an embodiment in which the shaft 165 has a single slot 167. In this embodiment, the catheter hub includes a corresponding single spline (not shown), and may be similar to the hub shown in FIGS. 2A and 2B with a single spline. In this embodiment, the shaft 165 includes an outer helical surface 170 that spirals downward into the slot 167. In this embodiment, duplicate connectors pins are not needed because the there is only one possible rotational alignment.

FIGS. 7A-7D show another embodiment in which the shaft 265 as four slots 267 spaced 90 degrees apart. In this embodiment, the hub includes four corresponding splines, and may be similar to the hub shown in FIGS. 2A and 2B with four splines spaced 90 degrees apart. Each orientating slot 267 has two beveled surfaces 270 that slope into the slot 267 from opposite sides of the slot 267. The beveled surfaces 270 of the slots 267 meet at sharp leading edges 275 centered between the adjacent slots 267. In this embodiment, the hub preferably has duplicate connector pins every 90 degrees since there are four possible rotational alignments between the rotator and the shaft in this embodiment.

The self-aligning connectors according to various embodiments of the invention provide several advantages. One advantage is that the rotational driving force to the imaging core is provide by the spline(s) in the slots(s), and not the electrical contacts of the catheter and shaft connector, thereby reducing mechanical stress on the contacts. Further, the rotary transformer or other coupling apparatus is housed in the MDU and not the catheter. Thus, a separate rotary transformer or other coupling apparatus does not need to be provided for each catheter, thereby reducing the per-unit cost of the catheters. In cases where the catheters are disposable, this reduces the cost of the disposable product. Further, the catheter can be assembled in two main sub-assemblies: the imaging core and the catheter body/hub. Each of these sub-assemblies can be tested separately prior to final assembly so that a defective sub-assembly can be discarded without scraping the entire assembly. After final assembly and testing, if one of the main sub-assemblies is defective, then the catheter can be disassembled, the defective part discarded, and the catheter reassembled with a replacement part replacing the defective sub-assembly.

The self-aligning connectors can be used in applications where precise rotational alignment of mating connectors is desired without the need for manual alignment. The self-alignment connectors are useful in cases where one or more parts rotate independently, alignment features end in random orientation, and there is a requirement that parts engage easily without the need for manual alignment.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A catheter system, comprising:
a catheter having a proximal end and a distal end, wherein the catheter comprises
a catheter body having a lumen;
a core received within the lumen of the catheter body;
a rotator coupled to a proximal end of the core, wherein the rotator is disposed at the proximal end of the catheter, and wherein the rotator is configured and arranged for rotating about an axis of rotation when coupled to a drive unit; and
at least one orienting feature, the at least one orienting feature comprising at least one elongated spline extending proximally from a side of the rotator along the axis of rotation of the rotator; and
a drive unit configured to receive the proximal end of the catheter, wherein the drive unit comprises
a rotatable shaft connector having a proximal end, a distal end, and a longitudinal length from the proximal end to the distal end, wherein the distal end of the shaft connector comprises a tubular distal portion comprising an inner layer and an outer layer disposed concentrically around at least a portion of the inner layer, wherein the inner layer comprises a distal edge that defines an opening configured and arranged to receive the rotator, wherein the rotatable shaft connector comprises a rotational axis extending along the longitudinal length of the rotatable shaft connector, wherein the outer layer comprises a distal edge with at least one sloping surface that slopes along at least a portion of the longitudinal length of the shaft connector, wherein the outer layer defines at least one orienting slot extending along the outer layer from the distal edge of the outer layer such that the at least one orienting slot is continuous with the at least one sloping surface, wherein the at least one orienting slot is configured and arranged such that when the opening of the inner layer receives the rotator the at least one orienting slot receives the at least one spline such that the at least one spline extends along a portion of the outer layer of the shaft connector that defines the at least one orienting slot, and wherein the rotator and core rotate with the shaft connector when the at least one spline is inserted into the at least one slot.

2. The catheter system of claim 1, wherein the sloping surface is configured to rotate the shaft connecter when a force in a direction substantially parallel to the rotational axis of the shaft connecter is exerted on the sloping surface.

3. The catheter system of claim 2, wherein the sloping surface spirals along a circumference of the shaft connector.

4. The catheter system of claim 2, wherein the sloping surface is substantially perpendicular to a circumference of the shaft connector.

5. The catheter system of claim 1, wherein the at least one orienting feature has a sharp leading edge.

6. The catheter system of claim 1, wherein the catheter comprises two orienting features, and the shaft connecter has two corresponding orienting slots.

7. The catheter system of claim 6, wherein the two orienting features are positioned on opposite sides of the rotator.

8. The catheter system of claim 6, wherein the shaft connector has two sloping surfaces coupled to opposite sides of each orienting slot.

9. The catheter system of claim 6, further comprising pairs of duplicate contacts on the rotator, wherein each pair of duplicate contacts are shorted together.

10. The catheter system of claim 9, wherein the contacts in each pair of duplicate contacts are orientated 180 degrees apart with respect to the rotational axis of the rotator.

11. The catheter system of claim 1, further comprising a motor housed within the drive unit and coupled to the proximal end of the shaft connector for rotating the shaft connector.

12. The catheter system of claim 1, further comprising a first set of electrical contacts on the rotator, and a second set of electrical contacts on the shaft connector, wherein the first set of contacts are configured to engage the second set of contacts when the at least one orienting feature is inserted into the at least one slot of the shaft connector.

13. The catheter system of claim 12, wherein the first set of contacts comprises connector pins, and the second set of contacts comprises sockets.

14. The catheter system of claim 13, wherein the sockets are housed within the shaft connector and are accessible through the opening in the shaft connector.

15. The catheter system of claim 1, wherein the core comprises a drive cable connected to the rotator and an ultrasound transducer connected to a distal end of the core.

16. The catheter system of claim 1, further comprising a stamped shaft coupled between the rotator and the proximal end of the core, wherein the stamped shaft is stamped around the proximal end of the core.

17. The catheter system of claim 1, further comprising a hub housing coupled to the catheter body, wherein the rotator is rotatably housed within the hub housing, and the drive unit has a port configured to receive the hub housing therein.

18. The catheter system of claim 17, further comprising a locking mechanism for locking the hub housing of the catheter to the drive unit.

19. The catheter system of claim 1, further comprising an electrical coupling apparatus housed within the drive unit and coupled to the shaft connector.

20. The catheter system of claim 19, wherein the coupling apparatus comprises a rotary transformer.

21. In a system including a drive unit having a rotatable shaft connector with a proximal end, a distal end, and a longitudinal length from the proximal end to the distal end, wherein the distal end of the shaft connector comprises a tubular distal portion comprising an inner layer and an outer layer disposed concentrically around at least a portion of the inner layer, wherein the inner layer comprises a distal edge that defines an opening, wherein the outer layer of the rotatable shaft connector defines at least one orienting slot, and wherein a catheter having a proximal end and a distal end is configured and arranged to mate with the drive unit, the catheter comprising:
a catheter body having a lumen;
a core received within the lumen of the catheter body;
a rotator coupled to a proximal end of the core, wherein the rotator is disposed at the proximal end of the catheter, and wherein the rotator is configured and arranged for at least partial insertion into the opening of the shaft connector and for rotation about an axis of rotation when mated with the drive unit; and
at least one orienting feature, the at least one orienting feature comprising at least one elongated spline extending proximally from a side of the rotator along the axis of rotation of the rotator;
wherein the rotatable shaft connector defines a rotational axis extending along the longitudinal length of the rotatable shaft connector;
wherein the outer layer of the rotatable shaft connector comprises a distal edge with at least one sloping surface that slopes along at least a portion of the longitudinal length of the shaft connector;
wherein the at least one orienting slot extends along the outer layer from the distal edge of the outer layer such that the at least one orienting slot is continuous with the at least one sloping surface;
wherein the at least one orienting slot is configured and arranged such that when the opening of the inner layer receives the rotator the at least one orienting slot receives the at least one spline such that the at least one spline extends along a portion of the outer layer of the shaft connector that defines the at least one orienting slot, and wherein the rotator and core are adapted to rotate with the shaft connector when the catheter is mated with the drive unit.

22. The catheter of claim 21, wherein the at least one orienting feature includes a sharp leading edge.

23. The catheter of claim 21, wherein the catheter comprises two orienting features adapted to mate with two orienting slots.

24. The catheter of claim 23, wherein the two orienting features are positioned on opposite sides of the rotator.

25. The catheter of claim 24, wherein the orienting features are adapted to slide along the sloping surfaces.

26. The catheter of claim 25, further comprising pairs of duplicate contacts on the rotator, wherein each pair of duplicate contacts are shorted together.

27. The catheter of claim 26, wherein the contacts in each pair of duplicate contacts are orientated 180 degrees apart with respect to the rotational axis of the rotator.

28. The catheter of claim 21, wherein the core comprises a drive cable connected to the rotator and an ultrasound transducer connected to a distal end of the core.

29. The catheter of claim 21, further comprising a stamped shaft coupled between the rotator and the proximal end of the core, wherein the stamped shaft is stamped around the proximal end of the core.

30. The catheter system of claim 1, wherein the at least one orienting slot extends lengthwise from the distal edge of the outer layer in a direction that is parallel to the rotational axis of the rotatable shaft connector.

31. The catheter of claim 21, wherein the at least one orienting slot extends lengthwise along the outer layer from the distal edge of the outer layer in a direction that is parallel to the rotational axis of the rotatable shaft connector.

* * * * *